(12) United States Patent
Williams et al.

(10) Patent No.: US 6,509,028 B2
(45) Date of Patent: Jan. 21, 2003

(54) METHODS AND COMPOSITIONS FOR TREATING PAIN OF THE MUCOUS MEMBRANE

(75) Inventors: Robert O. Williams, Austin, TX (US); Feng Zhang, Austin, TX (US); John J. Koleng, Austin, TX (US); Gavril W. Pasternak, New York, NY (US); Yuri A. Kolesnikov, Tenafly, NJ (US)

(73) Assignee: EpiCept Corporation, Englewood Cliffs, NJ (US)

( * ) Notice: Subject to any disclaimer, the term of this patent is extended or adjusted under 35 U.S.C. 154(b) by 0 days.

(21) Appl. No.: 10/172,455

(22) Filed: Jun. 17, 2002

(65) Prior Publication Data

US 2002/0192288 A1 Dec. 19, 2002

Related U.S. Application Data

(63) Continuation of application No. 09/888,466, filed on Jun. 25, 2001, now abandoned.
(60) Provisional application No. 60/222,164, filed on Jun. 26, 2000.

(51) Int. Cl.[7] ............................ A61F 13/00; A61K 9/70; A61K 9/14

(52) U.S. Cl. ....................... 424/434; 424/443; 424/486; 514/817; 514/818

(58) Field of Search ................................ 424/489, 434, 424/435, 443, 444, 445, 446, 447, 448, 449; 514/716, 626, 772, 817, 818, 900

(56) References Cited

U.S. PATENT DOCUMENTS

| | | |
|---|---|---|
| 4,051,234 A | 9/1977 | Gieske et al. |
| 4,226,848 A | 10/1980 | Nagai et al. |
| 4,704,406 A | 11/1987 | Stanislaus et al. |
| 4,764,378 A | 8/1988 | Keith et al. |
| 4,855,142 A | 8/1989 | Fankhauser et al. |
| 4,900,552 A | 2/1990 | Sanvordeker et al. |
| 5,219,861 A | 6/1993 | Kanematsu et al. |
| 5,225,196 A | 7/1993 | Robinson |
| 5,292,362 A | 3/1994 | Bass et al. |
| 5,395,318 A | 3/1995 | Kaprelian |
| 5,458,879 A | 10/1995 | Singh et al. |
| 5,460,826 A | 10/1995 | Merrill et al. |
| 5,496,811 A | 3/1996 | Aviv et al. |
| 5,578,315 A | 11/1996 | Chien et al. |
| 5,589,840 A | 12/1996 | Elkhoury et al. |
| 5,593,695 A | 1/1997 | Merrill et al. |
| 5,629,011 A | 5/1997 | Illum |
| 5,635,540 A | 6/1997 | Edlich et al. |

(List continued on next page.)

FOREIGN PATENT DOCUMENTS

WO WO/00/03716 1/2000

OTHER PUBLICATIONS

Atanassoff et al., 1997, "The Effect of Intradermal Administration of Lidocaine and Morphine on the Response to Thermal Stimulation", Anest. Analg. 84:1340–1343.
de Vries et al., 1991, "Developments in Buccal Drug Devlivery", Critical Reviews in Therapeutic Drug Carrier Systems, 8(3):271–303.
Harris et al., 1992, "Drug Dellivery via the Mucous Membranes of the Oral Cavity", J. of Pharm. Sciences 81(1):1–10.
Juninger HE, 1991, "Mucoadhesive Hydrogels", Pharm. Ind. 53(11):1056–1065.
Kolesnikov Y, 1999, "Topical opioids in mice: analgesia and reversal of tolerance by a topical N–methyl–D–aspartate antagonist", J Pharmacol Exp Ther. 290(1):247–52.
Kolesnikov Y, 2000, "Analgesic synergy between topical lidocaine and topical opioids", J Pharmacol Exp Ther. 295(2):546–51.
Lehr et al., 1992, "Visualization studies of the mucoadhesive interface", J. of Controlled Release, 18:249–260.
Likar R, 1998, "Peripheral morphine analgesia in dental surgery", Pain. 76(1–2):145–50.
Lockhart et al., 1981, "Alterations in the Oral Mucosa Caused by Chemotherapeutic Agents", J. Dermatol. Surg. Oncol. 7(12):1019 1025.
McQuinn et al., 1995, "Sustained oral muscosal delivery in human volunteers of buprenorphine from a thin non–eroding mucoadhesive polymeric disk", J. of Controlled Release 34:243–250.
Rossi et al., 1994, "$\mu$ and $\delta$ opioid synergy between the periaqueductal gray and the rostro–ventral medulla", Brain Res. 665:85–93.
Rottenberg et al., 1991, "Development and Testing of Bioadhesive, Fluoride–containing Slow Release Tablets for Oral Use", J. Pharm. Pharmacol. 43:457–464.
Salto et al., 1998, "Interaction of Intrathecally Infused Morphine and Lidocaine in Rats (Part II)", Anesthesiology 89:1464–1470.
Sonis et al., "Oral Complications of Cancer Chemotherapy in Pediatric Patients", 122–128.
Sonis et al., 1991, Prevention and Management of Oral Mucositis Induced by Antineoplastic Therapy 5:11–22.
Sonis et al., 1990, "An animal model for mucositis induced by cancer chemotherapy", Oral Surg. Oral Med. Oral Pathol. 69:437–44.
Stein et al., 1997, "Peripheral morphine analgesia", Pain. 71(2):119–21.

*Primary Examiner*—Thurman K. Page
*Assistant Examiner*—Blessing Fubara
(74) *Attorney, Agent, or Firm*—Pennie & Edmonds LLP

(57) ABSTRACT

Compositions useful for long-lasting pain relief from mucosal damage, such as mucosal inflamation, abrasions, ulcerations, lesions, trauma and incisions, without significant systemic absorption. The compositions of the invention are particularly suitable for application to the mucous membrane of the nasal cavity and buccal cavity. To relieve pain, the compositions or the invention are topically applied directly to the affected area.

31 Claims, No Drawings

U.S. PATENT DOCUMENTS

| | | |
|---|---|---|
| 5,744,458 A | 4/1998 | Kruse et al. |
| 5,747,060 A | 5/1998 | Sackler et al. |
| 5,760,023 A | 6/1998 | Farrar et al. |
| 5,798,093 A | 8/1998 | Farrar et al. |
| 5,811,078 A | 9/1998 | Maycock et al. |
| 5,814,330 A | 9/1998 | Putteman et al. |
| 5,817,625 A | 10/1998 | Haley |
| 5,834,478 A | 11/1998 | Ito |
| 5,846,971 A | 12/1998 | Sangekar et al. |
| 5,849,322 A | 12/1998 | Ebert et al. |
| 5,849,761 A | 12/1998 | Yaksh |
| 5,849,762 A | 12/1998 | Farrar et al. |
| 5,855,907 A | 1/1999 | Peyman |
| 5,866,143 A | 2/1999 | Elkhoury |
| 5,876,744 A | 3/1999 | Della Valle et al. |
| 5,885,597 A | 3/1999 | Botknecht et al. |
| 5,900,247 A | 5/1999 | Rault et al. |
| 5,906,810 A | 5/1999 | Turner |
| 5,908,846 A | 6/1999 | Bundgaard et al. |
| 5,922,340 A | 7/1999 | Berde et al. |
| 5,942,243 A | 8/1999 | Shah |
| 5,942,251 A | 8/1999 | Merkus |
| 5,948,430 A | 9/1999 | Zerbe et al. |
| 5,955,097 A | 9/1999 | Tapolsky et al. |
| 5,958,379 A | 9/1999 | Regenold et al. |
| 5,972,906 A | 10/1999 | Asculai et al. |
| 5,972,932 A * | 10/1999 | Benvenga et al. .......... 514/220 |
| 5,976,573 A | 11/1999 | Kim |
| 5,989,535 A | 11/1999 | Nayak |
| 5,993,846 A | 11/1999 | Friedman et al. |
| 6,031,007 A * | 2/2000 | Brodin et al. ............... 514/716 |
| 5,662,924 A | 9/1997 | Rhodes |
| 5,667,773 A | 9/1997 | Farrar et al. |
| 5,667,805 A | 9/1997 | Merrill et al. |
| 5,686,112 A | 11/1997 | Liedtke |
| 5,713,852 A | 2/1998 | Anthony et al. |

* cited by examiner

METHODS AND COMPOSITIONS FOR TREATING PAIN OF THE MUCOUS MEMBRANE

This is a continuation of application Ser. No. 09/888,466, filed Jun. 25, 2000, now Abandon.

This application claims the benefit of U.S. Provisional patent application Ser. No. 60/222,164, filed Jun. 26, 2000, hereby incorporated by reference herein in its entirety.

FIELD OF THE INVENTION

The invention relates to methods and compositions for treating the pain associated with mucosal damage, such as inflamation, abrasions, ulcerations, lesions, incisions, and trauma.

BACKGROUND OF THE INVENTION

The term mucous membrane refers to the moist linings of the buccal cavity, nasal cavity, gastrointestinal tract, respiratory tract, conjunctiva, vagina, colon, urinary bladder, and urethra (Forstner et al., 1973 *J. Cell. Sci.* 12:585; Peppas et al., 1985 *J. Control. Release* 2:257; Lehr et al., 1992 *J. Control Release* 18:249; Spiro, 1970 *Ann. Rev. Biochem.* 39:599; Lebat-Robert et al., 1979 *Path. Biol.* 24:241). The normally smooth, moist, and pink buccal mucosa is very sensitive and inflamation or ulceration (oral mucositis) causes severe pain. Dental surgery, such as root canal and tooth extraction can also severely damage the buccal mucosa causing severe pain. Moreover, oral mucositis and dental surgery can induce secondary conditions, such as weight loss and dehydration from reluctance to eat or drink, infection (bacterial, fungal, and viral), fever, nausea, and diarrhea.

Oral mucositis has a variety of causes, for example, bacterial infections, such as streptococci; viral infections, such as herpes simplex virus; fungal infections; side effects of systemic diseases; vitamin deficiency; iron deficiency; cheek biting; mouth breathing; jagged teeth; orthodontic appliances; ill-fitting dentures; excessive use of alcohol or tobacco; thermally-hot foods; spicy foods; and as a side effect of medication. Severely-painful oral mucositis is a symptom endured by almost all chemotherapy patients. Mucositis symptoms peak 7 to 10 days following chemotherapy, and gradually recede over the following two weeks. For a discussion of the causes and symptoms of mucositis, see *The Merck Manuel, Fifteenth Edition,* Merck Sharp & Dohme Research Laboratories, Rahway, N.J., (1987) pp. 2322–2320.

Topical application of local anesthetics can provide some relief of oral-mucositis and dental-surgery pain but absorption through the mucous membranes occurs rapidly, and pharmaceuticals applied to the mucous membrane for their local effect sometimes cause systemic toxicity (*Goodman and Gilman's The Pharmacological Basis of Therapeutics* 9th ed. J. G. Harman and L. E. Limird Eds., McGraw-Hill New York 1996 p. 8) especially with the higher doses required for adequate pain relief. Systemic absorption is even more likely when the mucous membrane is ulcerated or inflamed. Thus, with traditional anesthetic compositions for mucositis, e.g., 2 percent lidocaine oral rinse or 5% lidocaine ointment, systemic toxicity limits the dosage and so adequate pain relief is difficult to achieve. Other less toxic pain relieving compositions, such as rinses comprising hydrogen peroxide and sodium bicarbonate are less effective at reducing pain. An additional problem with oral rinses is, that following application, the action of swallowing and saliva reduces the concentration of active agent on the affected area, thus oral rinses comprising local anesthetics have a low duration of activity.

In summation, a long-lasting, non-toxic anesthetic composition effective for amelioration of the severe pain induced by mucosal damage, such as mucositis and dental surgery, is needed.

SUMMARY OF THE INVENTION

In one aspect, the invention provides compositions and methods that provide long-lasting local anesthesia and effective pain relief. The compositions of the invention can be topically applied to the affected area, for example, via a dose-metered applicator adapted for spraying or adapted for use with a cannula. When topically applied, the compositions of the invention provide a powerful local-anesthetizing effect, in spite of low anesthetic concentration. Hence, the compositions of the invention provide significant pain relief with low systemic absorption and, therefore, low systemic toxicity. The compositions of the invention, in addition to the ability to remain on the affected area for extended periods, hydrate and soothe.

In one embodiment, the compositions of the invention can be topically applied directly to the affected area to alleviate pain in a subject on any area of a subject's body.

In another embodiment, the compositions of the invention are useful for topical application to a subject's mucous membrane, to induce a long-lasting local-anesthetic effect, thereby relieving pain from mucositis, such as mucosal inflammation, abrasions, ulcerations, and lesions, without significant systemic absorption.

In yet another embodiment, the compositions of the invention are useful for topical application to the site of dental surgery, such as root-canal or tooth-extraction surgery, to induce a long-lasting local-anesthetic effect, thereby relieving the surgical pain, without significant systemic absorption.

In one more embodiment, the invention relates to compositions comprising a mucoadhesive, a local anesthetic or a pharmaceutically-acceptable salt thereof, and an opioid or a pharmaceutically-acceptable salt thereof. In a preferred embodiment, the compositions contain water and are sterile. In a more preferred embodiment, the compositions of the invention, further comprise a chelating agent and a preservative.

In another embodiment, the invention relates to a container adapted for topical application and containing a pharmaceutically-acceptable composition comprising a mucoadhesive, a local anesthetic or a pharmaceutically-acceptable salt thereof, and an opioid or a pharmaceutically-acceptable salt thereof. Preferably, the container is adapted for dose-metered application, such as a dose-metered pump for use with a spray applicator or cannula.

In still another embodiment, the invention relates to a method of inducing local anesthesia in a subject's mucosal membrane by topically applying a pharmaceutically-acceptable composition comprising a local anesthetic or a pharmaceutically-acceptable salt thereof and an opioid or a pharmaceutically-acceptable salt thereof to the subject's mucosal membrane. Preferably, the composition is applied to an area within the subject's buccal or nasal cavity. Preferably, the composition further comprises a mucoadhesive.

In yet another embodiment, the invention relates to a method of inducing local anesthesia in a subject by topically applying a composition comprising a mucoadhesive, a local anesthetic or a pharmaceutically-acceptable salt thereof, and an opioid or a pharmaceutically-acceptable salt thereof to a subject. Preferably, the composition is applied to a mucosal surface of the subject, for example, an area within the subject's buccal or nasal cavity.

These and other features, aspects, and advantages of the invention will become better understood with reference to the following detailed description, examples, and appended claims.

DETAILED DESCRIPTION OF THE INVENTION

The phrase "pharmaceutically-acceptable salt(s)," as used herein includes but is not limited to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically-acceptable acid addition salts of such basic compounds are those that form non-toxic acid addition salts, i.e., salts containing pharmacologically acceptable anions, including, but not limited to, sulfuric, citric, maleic, acetic, oxalic, hydrochloride, hydrobromide, hydroiodide, nitrate, sulfate, bisulfate, phosphate, acid phosphate, isonicotinate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts.

Compounds included in the present compositions that include an amino moiety may form pharmaceutically-acceptable salts with various amino acids, in addition to the acids mentioned above. Compounds, included in the present compositions, that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts. For a review on pharmaceutically-acceptable salts see Berge et al., 1977 *J. Pharm. Sci.*, 66:1, incorporated herein by reference.

As used herein the term "opioid" means all agonists and antagonists of opioid receptors, such as mu ($\mu$), kappa ($\kappa$), and delta ($\delta$) opioid receptors and subtypes thereof. For a discussion of opioid receptors and subtypes see *Goodman and Gilman's The Pharmacological Basis of Therapeutics* 9th ed. J. G. Harman and L. E. Limird Eds., McGraw-Hill New York:1996 pp. 521–555, incorporated herein by reference. The opioid can be any opioid receptor agonist or antagonist known or to be developed. Preferred opioids interact with the $\mu$-opioid receptor, the $\kappa$-opioid receptor, or both. Preferably, the opioid is an opioid-receptor agonist.

Examples of suitable opioids for use with the invention include, but are not limited to, alfentanil, allylprodine, alphaprodine, anileridine, benzylmorphine, benzitramide, nor-binaltorphimine, bremazocine, buprenorphine, butorphanol, clonitazene, codeine, CTOP, DAMGO, desomorphine, dextromoramide, dezocine, diampromide, dihydrocodeine, dihydrocodeine enol acetate, dihydromorphine, dimenoxadol, dimepheptanol, dimethylthiambutene, dioxaphetyl butyrate, dipipanone, diprenorphine, DPDPE, eptazocine, ethoheptazine, ethylketocyclazocine, ethylmethylthiambutene, etonitazene, etorphine, fentanyl, hydrocodone, hydromorphone, hydroxypethidine, isomethadone, ketobemidone, levorphanol, lofentanil, loperamide, meperidine, meptazinol, metazocaine, methadone, metopon, morphine, myrophine, nalbuphine, naltrindole, benzoylhydrazone, naltrexone, narceine, nicomorphine, norlevorphanol, normethadone, normorphine, norpipanone, opium, oxycodone, oxymorphone, papaveretum, papaverine, pentazocine, phenadoxone, phenazocine, phenoperidine, piminodine, pirtramide, proheptazine, promedol, propiram, propoxyphene, remifentanil, spiradoline, sufentanil, tilidine, U50,488, and U69,593, amiphenazole, cyclazocine, levallorphan, nalmefene, nalorphine, naloxone, and naltrexone or pharmaceutically-acceptable salts thereof, or mixtures thereof.

Examples of peptide opioids include, but are not limited to, Tyr-Gly-Gly-Phe-Leu ([Leu$^5$]enkephalin), Tyr-Gly-Gly-Phe-Met ([Met$^5$]enkephalin), Tyr-Gly-Gly-Phe-Leu-Arg-Arg-Ile-Arg-Pro-Lys-Leu-Lys-Trp-Asp-Asn-Gln (DynorphinA), Tyr-Gly-Gly-Phe-Leu-Arg-Arg-Gln-Phe-Lys-Val-Val-Thr (Dynorphin B), Tyr-Gly-Gly-Phe-Leu-Arg-Lys-Tyr-Pro-Lys ($\alpha$-Neoendorphin), Tyr-Gly-Gly-Phe-Leu-Arg-Lsy-Tyr-Pro ($\beta$-Neoendorphin), Tyr-Gly-Gly-Phe-Met-Thr-Ser-Glu-Lys-Ser-Gln-Thr-Pro-Leu-Val-Thr-Leu-Phe-Lys-Asn-Ala-Ile-Ile-Lys-Asn-Ala-Tyr-Lys-Lys-Gly-Glu ($\beta_h$-Endorphin), [D-Ala$^2$,MePhe$^4$Gly(ol)$^5$]enkephalin (DAMGO), [D-Pen$^2$,D-Pen$^5$]enkephalin (DPDPE), [D-Ser$^2$, Leu$^5$]enkephalin-Thr$^6$ (DSLET), [D-Ala$^2$,D-Leu$^5$] enkephalin (DADL), D-Phe-Cys-Tyr-D-Trp-Orn-Thr-Pen-Thr-NH$_2$(CTOP), [D-Ala$^2$,N-MePhe$^4$,Met(O)$^5$-ol] enkephalin (FK-33824), Tyr-D-Ala-Phe-Asp-Val-Val-Gly-NH$_2$ ([D-Ala$^2$]Deltorphin 1), Tyr-D-Ala-Phe-Glu-Val-Val-Gly-NH$_2$ ([D-Ala$^2$Glu$^4$]Deltorphin (Deltorphin II)), Tyr-Pro-Phe-Pro-NH$^2$ (Morphiceptin), Tyr-Pro-MePhe-D-Pro-NH$^2$ (PL-017), [D-Ala$^2$,Leu$^5$,Cys$^6$]enkephalin (DALCE) or pharmaceutically-acceptable salts thereof, or mixtures thereof Preferred opioids include morphine, loperamide and loperamide derivatives such as those disclosed in U.S. Pat. Nos. 5,763,445; 5,981,513; 5,869,521; 5,744,458; 5,760,023; 5,798,093; 5,849,762; 5,811,078; 6,004,964; 5,962,477; 5,688,955; 5,888,494; 5,646,151; and 5,667,773 (all of which patents are incorporated by reference herein), or pharmaceutically-acceptable salts thereof, or mixtures thereof. The most preferred opioid is morphine or a pharmaceutically-acceptable salt thereof.

As used herein, the term "local anesthetic" means any drug that provides local numbness or analgesia or any drug that provides a regional blockage of nociceptive pathways (afferent and/or efferent) and that is not an agonist or an antagonist of an opioid receptors. The local anesthetic can be any local anesthetic known or to be developed. Examples of local anesthetics suitable for use with the invention include: ambucaine, amolanone, amylcaine, benoxinate, benzocaine, betoxycaine, biphenamine, bupivacaine, butacaine, butamben, butanilicaine, butethamine, butoxycaine, carticaine, chloroprocaine, cocaethylene, cocaine, cyclomethycaine, dibucaine, dimethisoquin, dimethocaine, diperodon, dyclonine, ecogonidine, ecogonine, euprocin, fenalcomine, formocaine, hexylcaine, hydroxyteteracaine, isobutyl p-aminobenzoate, leucinocaine, levoxadrol, lidocaine, mepivacaine, meprylcaine, metabutoxycaine, methyl chloride, myrtecaine, naepaine, octacaine, orthocaine, oxethazaine, parenthoxycaine, phenacaine, phenol, piperocaine, piridocaine, polidocanol, pramoxine, prilocaine, procaine, propanocaine, proparacaine, propipocaine, propoxycaine, pseudococaine, pyrrocaine, ropivacaine, salicyl alcohol, tetracaine, tolycaine, trimecaine, zolamine, or pharmaceutically-acceptable salts thereof, or mixtures thereof.

The amide and ester type local anesthetics are preferred. Amide type local anesthetics are characterized by an amide functionality, while ester type local anesthetics contain an ester functionality. Preferred amide type local anesthetics, include lidocaine, bupivacaine, prilocaine, mepivacaine, etidocaine, ropivacaine, dibucaine, and pharmaceutically-acceptable salts thereof and mixtures thereof. Preferred ester type local anesthetics include tetracaine, procaine, benzocaine, chloroprocaine, and pharmaceutically-acceptable salts thereof and mixtures thereof. The most preferred local anesthetic is lidocaine. The meaning of "local anesthetic" also encompasses drugs not traditionally associated with local anesthetic properties but which have a local-anesthetic effect, for example, non-narcotic analgesics, such as, acetylsalicylic acid, ketoprofen, piroxicam, diclofenac, indomethacin, ketorolac, Vioxx®, and Celebrex®. Furthermore, in order to improve the effectiveness and tolerance of the present topically-effective therapy, local anesthetics with different pharmacodynamics and pharmacokinetics may be combined in a composition of the invention. A preferred combination of local anesthetics is lidocaine and prilocaine and another preferred combination is lidocaine and tetracaine.

As used herein, the term "local delivery" of a therapeutic, means topical application of the therapeutic to a subject, whereafter a therapeutically-effective amount of the therapeutic is absorbed in the immediate application area, preferably, without significant absorption into the blood stream.

As used herein, a "therapeutically-effective amount" of the compositions of the invention means the amount required to induce a local-anesthetic effect or numbness sufficient to ameliorate pain induced by ulceration, inflamation, or lesions of the buccal or nasal membrane or other mucous membranes or the pain associated with mucosal trauma, such as dental surgery. Preferably, the active agents of the composition are not absorbed systemically.

As used herein, the term "subject" means any animal, preferably a mammal, more preferably a human.

As used herein the term "mucoadhesive" means a natural or synthetic substance, e.g., gels, pastes, macromolecules, polymers, and oligomers, or mixtures thereof, that can adhere to a subject's mucous membrane for a period of time sufficient to locally deliver a therapeutically-effective amount of a composition of the invention to a subject. Adhesion of mucoadhesives to the mucous membrane occurs primarily via secondary chemical bonds, such as hydrogen bonding and Van der Waal forces (Tabor et al., 1977 *J. Colloid Interface Sci.* 58:2 and Good 1977 *J. Colloid Interface Sci.* 59:398). Mucoadhesive substances often form viscous aqueous solutions. The composition itself does not need to be mucoadhesive, as long as it can form a mucoadhesive gel upon on the contact with the mucous membrane. For example, gellan gum itself is a very weak mucoadhesive. On contact with the buccal membrane, gellan gum can interact with the ions in the mucous membrane and form an adhesive gel layer. According to the invention, mucoadhesives possess binding properties that may be distinguished from non-mucoadhesives by comparing the degree of adhesion to a mucosal surface. For example, comparison of a potential mucoadhesive with a control emulsion of comparable viscosity prepared without mucoadhesive properties, e.g., a starch solution. At similar viscosities, the emulsion prepared with the mucoadhesive will bind to the mucosal surface more strongly than will the control emulsion, preferably at least 25% greater mucosal binding than the control emulsion, more preferably at least 50% greater, still more preferably at least 100% greater mucosal binding. Either mechanical binding to mucous membrane per se or the degree of biological effect of a drug delivered may be used as a measurement parameter for mucoadhesion. This test may be used to distinguish preferred mucoadhesives. Substances can be screened for their ability to be used as mucoadhesives for local delivery of compositions of the invention according to the methodology described in Smart et al., 1982 *J. Pharm. Pharmacol.* 34:70P and Smart et al., 1984 J. Pharm. Pharmacol. 36:295, which methodology comprises estimating values of adhesive strength between the substance and the mucous membrane. Preferably, the mucoadhesive is water soluble, such that at least 1% by weight of the mucoadhesive is soluble in water at 25° C. In a preferred embodiment, the mucoadhesive will exhibit non-Newtonian fluid properties, i.e., the viscosity decreases with increasing shear forces. Accordingly, the viscosity of the composition can be modulated by altering the shear forces present when the composition is applied to a surface. A composition with non-Newtonian fluid properties, becomes less viscous when shaken or atomized, then, upon standing, returns to its original viscosity.

Examples of mucoadhesives for use in the present invention include, but are not limited to, pectin, alginic acid, chitosan, hyaluronic acid, polysorbates, such as polysorbate-20, -21, -40, -60, -61, -65, -80, -81, -85; poly (ethyleneglycol), such as PEG-7, -14, -16, -18, -55, -90, -100, -135, -180, -4, -240, -6, -8, -9, -10, -12, -20, or -32; oligosaccharides and polysaccharides, such as gellan, carrageenan, xanthan gum, gum Arabic, and dextran; cellulose esters and cellulose ethers; modified cellulose polymers, such as carboxymethylcellulose, hydroxyethylcellulose, hydroxypropyl methylcellulose, hydroxyethyl ethylcellulose; polyether polymers and oligomers, such as polyoxyethylene; condensation products of poly(ethyleneoxide) with various reactive hydrogen containing compounds having long hydrophobic chains (e.g. aliphatic chains of about 12 to 20 carbon atoms), for example, condensation products of poly(ethylene oxide) with fatty acids, fatty alcohols, fatty amides, polyhydric alcohols; polyether compounds, such as poly(methyl vinyl ether), polyoxypropylene of less than 10 repeating units; polyether compounds, such as block copolymers of ethylene oxide and propylene oxide; mixtures of block copolymers of ethylene oxide and propylene oxide with other excipients, for example, pluronic lethicin organogel (see 1997 *International Journal of Pharmaceutical Compounding* 1:71); poly (vinyl alcohol); polyacrylamide; hydrolyzed polyacrylamide; poly(vinyl pyrrolidone); poly(methacrylic acid); poly (acrylic acid) or cosslinked polyacrylic acid, such as carbomer, i.e., a homopolymer of acrylic acid crosslinked with either an allyl ether of pentaerythritol, an allyl ether of sucrose, or an allyl ether of propylene (e.g., Acrisint® 400, 410, or 430 commercially available from 3V Inc. Weehawkin, N.J.); Orabase® (i.e., a mixture of gelatine, pectin and sodium carboxymethyl cellulose in a plasticized hydrocarbon gel, commercially available from Hoyt laboratories, Needhm, Mass.); Carafate® (sulfated sucrose and aluminum hydroxide, commercially available from Marion Laboratories, Inc., Kansas City, Mont.). The block copolymers of ethylene oxide and propylene oxide are particularly preferred. Preferred block copolymers of ethylene oxide and propylene oxide are represented by formula I below:

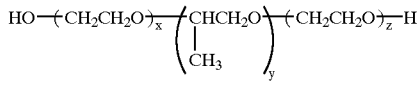
                                                                I

Wherein x is an integer having an average value within the range of from about 2 to about 128; y is an integer having an average value within the range of from about 14 to about 80; and z is an integer having an average value within the range of from about 2 to about 128. Preferably, x and y are about equal. More preferred block copolymers of ethylene oxide and propylene oxide, falling within the genus represented by formula I, are shown in Table 1 below.

TABLE 1

| Name | Trade Name | approximate value of x | approximate value of y | approximate value of z |
|---|---|---|---|---|
| Poloxamer 101 | Pluronic ® L-31 | 2 | 16 | 2 |
| Poloxamer 105 | Pluronic L-35 | 11 | 16 | 11 |
| Poloxamer 108 | Pluronic F-38 | 46 | 16 | 46 |
| Poloxamer 122 | Calgene Nonionic ® 1042-L | 5 | 21 | 5 |
| Poloxamer 123 | Pluronic L-43 | 7 | 21 | 7 |
| Poloxamer 124 | Pluronic L-44 | 11 | 21 | 11 |
| Poloxamer 181 | Pluronic L-61 | 3 | 30 | 3 |
| Poloxamer 182 | Pluronic L-62 | 8 | 30 | 8 |
| Poloxamer 183 | Calgene Nonionic 1063-L | 10 | 30 | 10 |
| Poloxamer 184 | Pluronic L-64 | 13 | 30 | 13 |
| Poloxamer 185 | Pluronic P-65 | 19 | 30 | 19 |
| Poloxamer 188 | Pluronic F-68 | 75 | 30 | 75 |
| Poloxamer 212 | Calgene Nonionic 1072-L | 8 | 35 | 8 |
| Poloxamer 215 | Calgene Nonionic 1075-P | 24 | 35 | 24 |
| Poloxamer 217 | Pluronic F-77 | 52 | 35 | 52 |
| Poloxamer 231 | Pluronic L-81 | 6 | 39 | 6 |
| Poloxamer 234 | Pluronic P-84 | 22 | 39 | 22 |
| Poloxamer 235 | Pluronic P-85 | 27 | 39 | 27 |
| Poloxamer 237 | Pluronic F-87 | 62 | 39 | 62 |
| Poloxamer 238 | Pluronic F-88 | 97 | 39 | 97 |
| Poloxamer 282 | Pluronic L-92 | 10 | 47 | 10 |
| Poloxamer 284 | Calgene Nonionic 1094-P | 21 | 47 | 21 |
| Poloxamer 288 | Pluronic F-98 | 122 | 47 | 122 |
| Poloxamer 331 | Pluronic L-101 | 7 | 54 | 7 |
| Poloxamer 333 | Puronic P-103 | 20 | 54 | 20 |
| Poloxamer 334 | Pluronic P-104 | 31 | 54 | 31 |
| Poloxamer 335 | Pluronic P-105 | 38 | 54 | 38 |
| Poloxamer 338 | Pluronic F-108 | 128 | 54 | 128 |
| Poloxamer 401 | Pluronic L-121 | 6 | 67 | 6 |
| Poloxamer 403 | Pluronic P-123 | 21 | 67 | 21 |
| Poloxamer 407 | Pluronic F-127 | 98 | 67 | 98 |

The most preferred mucoadhesive for use with the invention is poloxamer 407. The block copolymers of ethylene oxide and propylene oxide sold under the trade name Pluronic are commercially available, e.g., BASF (Washington, N.J.). The block copolymers of ethylene oxide and propylene oxide sold under the trade name Calgene are commercially available, e.g., Calgene Chemical, Inc. Skokie, Ill.

Preferably, when administered to a subject, the compositions of the invention are sterile.

Suitable preservatives include, but are not limited to, quaternary ammonium compounds, such as benzalkonium chloride, benzethonium chloride, cetrimide, dequalinium chloride, and cetylpyridinium chloride; mercurial agents, such as phenylmercuric nitrate, phenylmercuric acetate, and thimerosal; alcoholic agents, for example, chlorobutanol, phenylethyl alcohol, and benzyl alcohol; antibacterial esters, for example, esters of para-hydroxybenzoic acid; and other anti-microbial agents such as chlorhexidine, chlorocresol, and polymyxin.

Suitable chelating agents include, but are not limited to, deferoxamine, ditiocarb sodium, edetate calcium disodium, edetate disodium, edetate sodium, edetate trisodium, penicillamine, pentetate calcium trisodium, pentetic acid, succimer, trientin.

Preferably, the pH of the composition is within the range of from about 2 to about 9, more preferably, about 3 to about 7, even more preferably about 4 to about 5, and optimally about 4.5. Under acidic conditions, protonation permits H-bonding between the polymer and the mucin network, resulting in enhanced retention of the polymer in contact with a mucosal surface. The pH can be adjusted by adding an aqueous acid or base, dropwise to the composition until the desired pH is obtained. Any physiologically acceptable pH adjusting acids, bases or buffers are acceptable, e.g., acids, such as acetic, boric, citric, lactic, phosphoric, hydrochloric; bases, such as sodium hydroxide, sodium phosphate, sodium borate, sodium citrate, sodium acetate, sodium lactate, THAM (trishydroxymethylaminomethane); and buffers such as citrate/dextrose, sodium bicarbonate, ammonium chloride and mixtures thereof, preferably, 0.1 normal hydrochloric acid for a pH of less than 7 and 0.1 normal aqueous sodium hydroxide for a pH of greater than 7.

The composition of the invention can also comprise NMDA receptor antagonists including, but not limited to, dextromethorphan, dextrorphan, ketamine, pyroloquinolin quinone, cis-4-(phosphonomethyl)-2-piperidine carboxylic acid, MK801, memantine, D-methadone, or pharmaceutically-acceptable salts thereof.

The compositions of the invention can also include other excipients and pharmaceuticals. Examples of excipients that can be included in the topical compositions of the invention include, but are not limited to, antibiotics, analgesics, antifungal agents, non-steroidal anti-inflammatory agents, antitussive agents, expectorants, glucocorticoids, vitamins, antioxidants, flavoring agents, sweetening agents, iso-osmotic agents, moisturizers, emollients, buffering agents, solubilizing agents, penetration agents, protectants, surfactants, and propellants, and other conventional systemic or topical pain relief therapies, analgesics, and pharmaceuticals.

Examples of suitable antibiotics include, but are not limited to, aminoglycoside antibiotics; such as apramycin, arbekacin, bambermycins, butirosin, dibekacin, neomycin, neomycin undecylenate, netilmicin, paromomycin, ribostamycin, sisomicin, and spectinomycin; amphenicol antibiotics, such as azidamfenicol, chloramphenicol, florfenicol, and thiamphenicol; ansamycin antibiotics, such as rifamide and rifampin; carbacephems, such as loracarbef; carbapenems, such as biapenem and imipenem; cephalosporins, such as cefaclor, cefadroxil, cefamandole, cefatrizine, cefazedone, cefozopran, cefpimizole, cefpiramide, and cefpirome; cephamycins, such as cefbuperazone, cefmetazole, cefminox; monobactams, such as aztreonam, carumonam, and tigemonam; oxacephems, such as flomoxef, and moxalactam; penicillins, such as amdinocillin, amdinocillin pivoxil, amoxicillin, bacampicillin, benzylpenicillinic acid, benzylpenicillin sodium, epicillin, fenbenicillin, floxacillin, penamccillin, penethamate hydriodide, penicillin o-benethamine, penicillin 0, penicillin V, penicillin V benzathine, penicillin V hydrabamine, penimepicycline, and phencihicillin potassium; lincosamides, such as clindamycin, and lincomycin; macrolides, such as azithromycin, carbomycin, clarithomycin, dirithromycin, erythromycin, erythromycin acistrate; polypeptides, such as amphomycin, bacitracin, capreomycin, colistin, enduracidin, and enviomycin; tetracyclines, such as apicycline, chlortetracycline, clomocycline, and demeclocycline; 2,4-diaminopyrimidines, such as brodimoprim; nitrofurans, such as furaltadone, and furazolium chloride; quinolones and analogs, such as cinoxacin, ciprofloxacin, clinafloxacin, flumequine, and grepagloxacin; sulfonamides, such as acetyl sulfamethoxypyrazine, benzylsulfamide, noprylsulfamide, phthalylsulfacetamide, sulfachrysoidine, and sulfacytine; sulfones, such as diathymosulfone, glucosulfone sodium, and solasulfone; and others, such as cycloserine, mupirocin, tuberin.

Examples of suitable analgesics include, but are not limited to, aceclofenac, acetaminophen, acetaminosalol, acetanilide, acetylsalicylsalicylic acid, alclofenac, alminoprofen, aloxiprin, aluminum bis(acetylsalicylate), aminochlorthenoxazin, 2-amino-4-picoline, aminopropylon, aminopyrine, ammonium salicylate, amtohnetin guacil, antipyrine, antipyrine salicylate, antrafenine, apazone, aspirin, benorylate, benoxaprofen, benzpiperylon, benzydamine, bermoprofen, bromfenac, p-bromoacetanilide, 5-bromosalicylic acid acetate, bucetin, bufexamac, bumadizon, butacetin, calcium acetylsalicylate, carbamazepine, carbiphene, carsalam, chlorthenoxazin(e), choline salicylate, cinchophen, ciramadol, clometacin, clonixin, cropropamide, crotethamide, dexoxadrol difenamizole, diflunisal, dihydroxyaluminum acetylsalicylate, dipyrocetyl, dipyrone, emorfazone, enfenamic acid, epirizole, etersalate, ethenzamide, ethoxazene, etodolac, felbinac, fenoprofen, floctafenine, flufenamic acid, fluoresone, flupirtine, fluproquazone, flurbiprofen, fosfosal, gentisic acid, glafenine, ibufenac, imidazole salicylate, indomethacin, indoprofen, isofezolac, isoladol, isonixin, ketoprofen, ketorolac, p-lactophcnetide, lefetamine, lomoxicam, loxoprofen, lysine acerylsalicylate, magnesium acetylsalicylate, methotrimeprazine, metofoline, mofezolac, morazone, morpholine salicylate naproxen, nefopam, nifenazone, 5'-nitro-2'-propoxyacetanilide, parsalmide, perisoxal, phenacetin, phenazopyridine hydrochloride, phenocoll, phenopyrazone, phenyl acetylsalicylate, phenyl salicylate, phenyramidol, pipebuzone, piperylone, propacetamol, propyphenazone, ramifenazone, rimazolium metilsulfate, salacetamide, salicin, salicylamide, salicylamide o-acetic acid, salicylsulfuric acid, salsalate, salverine, simetride, sodium salicylate, suprofen, talniflumate, tenoxicam, terofenamate, tetrandrine, tinoridine, tolfenamic acid, tramadol, tropesin, viminol, xenbucin, and zomepirac.

Examples of suitable antifungal agents include, but are not limited to, polyenes, such as amphotericin b, candicidin, mepartricin, natamycin, and nystatin; allylamines, such as butenafine, and naftifine; imidazoles, such as bifonazole, butoconazole, chlordantoin, flutrimazole, isoconazole, ketoconazole, and lanoconazole; thiocarbamates, such as tolciclate, tolindate, and tolnaftate; triazoles, such as fluconazole, itraconazole, saperconazole, and terconazole; and others, such as bromosalicylchloranilide, buclosamide, calcium propionate, chlorphenesin, and ciclopirox; and others, such as azaserine, griseofulvin, oligomycins, neomycin undecylenate, pyrrolnitrin, siccanin, tubercidin, viridin.

Examples of suitable non-steroidal anti-inflammatory agents include, but are not limited to, aminoarylcarboxylic acid derivatives, such as enfenamic acid, etofenamate, flufenamic acid, isonixin, meclofenamic acid, mefenamic acid, niflumic acid, talniflumate, terofenamate, and tolfenamic acid; arylacetic acid derivatives, such as aceclofenac, acemetacin, alclofenac, amfenac, amtolmetin guacil, bromfenac, bufexamac, cinmetacin, clopirac, diclofenac sodium, etodolac, felbinac, fenclozic acid, fentiazac, glucametacin, ibufenac, indomethacin, isofezolac isoxepac, lonazolac, metiazinic acid, mofezolac, oxametacine, pirazolac, proglumetacin, sulindac, tiaramide, tolmetin, tropesin, and zomepirac; arylbutyric acid derivatives, such as bumadizon, butibufen, fenbufen, xenbucin; arylcarboxylic acids, such as clidanac, ketorolac, tinoridine; arylpropionic acid derivatives, such as alminoprofen, benoxaprofin, bermoprofen, bucloxic acid, carprofen, fenoprofen, flunoxaprofen, flurbiprofen, ibuprofen, ibuproxam, indoprofen, ketoprofen, loxoprofen, naproxen, oxaprozin, piketoprofin, pirprofen, pranoprofen, protizinic acid, suprofen, tiaprofenic acid, ximoprofen, and zaltoprofen; pyrazoles, such as difenamizole, and epirozole; pyrazolones, such as apazone, benzpiperylon, feprazone, mofebutazone, morazone, oxyphenbutazone, phenylbutazone, pipebuzone, propyphenazone, ramifenazone, suxibuzone, and thiazolinobutazone; salicylic acid derivatives, such as acetaminosalol, aspirin, benorylate, bromosaligenin, calcium acetylsalicylate, diflunisal, etersalate, fendosal, gentisic acid, glycol salicylate, imidazole salicylate, lysine acetylsalicylate, mesalamine, morpholine salicylate, 1-naphtyl salicylate, olsalazine, parsalmide, phenyl acetylsalicylate, phenyl salicylate, salacetamide, salicylamide o-acetic acid, salicylsulfuric acid, salsalate, sulfasalazine; thiazinecarboxamides, such as ampiroxicam, droxicam, isoxicam, lomoxicam, piroxicam, and tenoxicam; and others, such as ε-acetamidocaproic acid, s-adenosylmethionine, 3-amino-4-hydroxybutytic acid, amixetrine, bendazac, benzydamine, α-bisabolol, bucololome, difenpiramide, ditazol, emorfazone, fepradinol, guaiazulene, nabumetone, nimesulide, oxaceprol, paranyline, perisoxal, proquazone, superoxide dismutase, tenidap, and zilenton.

Examples of suitable antitussive agents include, but are not limited to, alloclamide, amicibone, benproperine, benzonatate, bibenzonium bromide, bromoform, butamirate, butethamate, caramiphen ethanedisulfonate, carbetapentane, chlophedianol, clobutinol, cloperastine, codeine, codeine methyl bromide, codeine n-oxide, codeine phosphate, codeine sulfate, cyclexanone, dimethoxanate, dropropizine, drotebanol, eprazinone, ethyl dibunate, ethylmorphine, fominoben, guaiapate, hydrocodone, isoaminile, levopropoxyphene, morclofone, narceine, mormethadone, noscapine, oxeladin, oxolamine, pholcodine, picoperine, pipazethate, piperidione, prenoxdiazine hydrochloride, racemethorphan, sodium dibunate, tipepidine, and zipeprol.

Example of suitable expectorants include, but are not limited to, ambroxol, ammonium bicarbonate, ammonium carbonate, bromhexine, calcium iodide, carbocysteine, guaiacol, guaiacol benzoate, guaiacolcarbonate, guaiacol phosphate, guaifenesin, guaithylline, hydriodic acid, iodinated glycerol, potassium guaiacolsulfonate, potassium iodide, sodium citrate, sodium iodide, storax, terebene, terpin, and trifolium.

Suitable glucocorticoids include, but are not limited to, 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, flucortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, and triamcinolone hexacetonide.

Suitable vitamins include, but are not limited to calcipotriene, calcitriol, ergosterol, 1α-hydroxycholecalciferol, vitamin $D_{2+}$, vitamin $D_{3+}$, ascorbic acid, calcium ascorbate, nicotinamide ascorbate, sodium ascorbate, α-carotene, β-carotene, δ-carotene, vitamin A, cobamamide, folic acid, hydroxocobalamin, sodium folate, vitamin $B_{12}$, menadiol, menadione, menadoxime, menaquinones, phylloquinone, vitamin $K_{5+}$, inositol, αtocopherol, γ-tocopherol, γ-tocopherol, vitamin E, vitamin E acetate, and vitamin U.

Examples of suitable anti-oxidants include, but are not limited to, ascorbic acid, sodium ascorbate, sodium bisulfite, sodium thiosulfate, 8-hydroxy quinoline, and N-acetyl cysterine.

Examples of suitable flavoring agents include, but are not limited to, oil of spearmint, peppermint, wintergreen, sassafras, clove, sage, eucalyptus, marjoram, cinnamon, lemon, and orange, and methyl salicylate.

Examples of suitable sweetening agents include, but are not limited to, sucrose, lactose, maltose, sorbitol, xylitol, sodium cyclamate, perillartine, AMP (aspartyl phenyl alanine, methyl ester), and saccharine.

The compositions of the present invention optionally can include an iso-osmotic agent which functions to prevent irritation of the mucosa by the composition. Examples of pharmaceutically-acceptable iso-osmotic agents which can be used include sodium chloride, dextrose, and calcium chloride.

Preferably, the amount of local anesthetic in the composition is within the range of from about 0.005 percent to about 2 percent of the total weight of the composition, more preferably, of from about 0.01 percent to about 0.5 percent of the total weight of the composition.

For treatment of oral mucositis, a preferred concentration of local anesthetic is from about 0.02 percent to about 0.1 percent of the total weight of the composition, more preferably, about 0.04 percent to about 0.08 percent. For treatment of more painful conditions, such as dental surgery (e.g., tooth extraction or root canal), a preferred concentration of local anesthetic is from about 0.1 percent to about 0.4 percent of the total weight of the composition, more preferably, about 0.2 percent to about 0.3 percent.

Preferably, the amount of opioid in the composition is within the range of from about 0.005 percent to about 3 percent of the total weight of the composition, more preferably, of from about 0.01 percent to about 2 percent, still more preferably, of from about 0.05 percent to about 1 percent of the total weight of the composition. For treatment of oral mucositis, a preferred concentration of opioid is from about 0.1 percent to about 0.3 percent of the total weight of the composition. For treatment of more painful conditions, such as dental surgery, a preferred concentration of opioid is from about 0.3 percent to about 0.8 percent of the total weight of the composition, more preferably, about 0.4 percent to about 0.5 percent.

Preferably, the amount of mucoadhesive in the composition is within the range of from about 0.1 percent to about 40 percent of the total weight of the composition, more preferably, of from about 10 percent to about 30 percent, and optimally, of from about 15 percent to about 25 percent of the total weight of the composition.

Preferably, the amount of water in the composition is within the range of from about 95 percent to about 10 percent of the total weight of the composition, more preferably, of from about 90 percent to about 50 percent, and optimally, of from about 85 percent to about 75 percent of the total weight of the composition.

When a chelating agent is used, preferably, it is present in an amount within the range of from about 0.005 percent to about 1 percent of the total weight of the composition, more preferably, of from about 0.01 percent to about 0.5 percent, still more preferably, of from about 0.05 percent to about 0.2 percent of the composition.

When a preservative is used, preferably, it is present in an amount within the range of from about 0.0001 percent to about 0.2 percent of the total weight of the composition, more preferably, of from about 0.0005 percent to about 0.1 percent, and optimally, of from about 0.001 percent to about 0.05 percent of the total weight of the composition.

To relieve pain from mucositis, the compositions or the invention are topically applied directly to the affected area. The compositions of the invention can be applied to the affected area of the mucous membrane in any conventional manner well known in the art, for example, as a mist via an aerosol applicator, by cannula, via a patch, by a dropper, or by an applicator stick, preferably as a mist, more preferably as a metered-dose mist. A mist can be sprayed onto the area to be treated via an aerosol container, pressurized or non-pressurized, preferably a non-pressurized pump. For more specific applications, a cannula can be used. The cannula can be attached to a pressurized or non-pressurized pump, preferably a non-pressurized pump.

A suitable non-pressurized pump for application of compositions of the invention can comprise a container, a valve, an actuator, and optionally a dip tube. The non-pressurized pump's container can be metal, such as a tin plated steel or aluminum, glass, or plastic. The valve's primary purpose is to regulate the flow of product from the container. It provides a means of discharging the desired amount. Suitable spray valves are described in *Remington's Pharmaceutical Sciences* 18th Edition, ed. Alfonso Gennaro, Mack Publishing Co. Easton, Pa., 1990 pp. 1703–1704, incorporated herein by reference. The actuator provides a means for releasing the contents from a pressurized container. Suitable actuators are described in *Remington's Pharmaceutical Sciences* 18th Edition, ed. Alfonso Gennaro, Mack Publishing Co. Easton, Pa., 1990 pp. 1704–1705, incorporated herein by reference.

Preferably, the metered pump is a VP 7 Screw-On Pump (90 μl, 18/415) commercially available from Valois of America, Inc. (Greenwich, Conn.). The VP 7 screw-on pump is manufactured from polyethylene and polypropylene. It is designed in a way such that the hydraulically opening clapper eliminates the use of any elastomeric gaskets in contact with the product. The pump has an annular dosing chamber, which fills only at the full return of the actuator to ensure full dosing and precision.

The preferred actuator is the 132C-BL GP4 BL long throat actuator commercially available from Valois Pharmaceuticals, Inc. Preferably, the actuator is manufactured from polyethylene and polypropylene and, preferably, contains a captive insert to provide a well-atomized spray pattern. The captive insert also reduces the dead volume in the actuator.

When a cannula is used, for application to a specific area rather than as a spray, the preferred actuator is a stainless-steel cannula of about 73 mm in length, for example, the 215 stainless-steel cannula commercially available from Valois Pharmaceuticals, Inc. Polyethylene or polypropylene cannulas can also be used.

The compositions of the invention can also be delivered to the buccal or nasal cavity via a patch that is applied adjacent to the area of skin to be treated. As used herein a "patch" comprises at least a composition of the invention and a covering layer, such that, the patch can be placed over the area to be treated. Preferably, the patch is designed to maximize local delivery and to minimize absorption into the circulatory system, reduce lag time, promote uniform absorption, and reduce mechanical rub-off. Suitable patches are described in *Transdermal and Topical Drug Delivery Systems*, Interpharm Press, Inc. p. 249–297, incorporated herein by reference. Suitable patches for buccal delivery of compositions of the invention is disclosed in U.S. Pat. Nos. 5,713,852 and 4,900,552, both of which are incorporated herein by reference.

The amount of the composition of the invention applied to the buccal or nasal passages will vary depending on the particular mucoadhesive, local anesthetic, and opioid used; the nature and severity of the mucosal lesion or inflamation being treated, and the subject. The composition should be applied to the affected area as recommended by a physician, preferably, as needed by the patient to relieve pain. For example, a dose of about 0.05 mg to about 4 mg morphine sulfate and 0.02 mg to about 3 mg of lidocaine hydrochloride in about 0.5 g to about 3 g of composition can be delivered to the affected area. When applying as a spray, a dose of about 2 mg morphine sulfate and about 1 mg lidocaine hydrochloride in about 1.5 g of composition can be delivered to the affected area. For more precise applications by cannula, a dose of about 2 mg morphine sulfate and about 1 mg lidocaine hydrochloride in about 0.4 g of composition can be delivered to the affected area.

In a preferred embodiment of administration, the dose is delivered with a spray actuator in about 8 to about 20 separate spray shots, more preferably about 16 spray shots, wherein each spray shot weighs about 50 mg to about 150 mg, more preferably about 100 mg. In another preferred embodiment of administration, the dose is delivered via cannula in about 4 spray shots, wherein each spray shot weighs about 100 mg.

Although the present invention has been described in considerable detail with reference to certain preferred embodiments, other embodiments are possible. Therefore, the spirit and scope of the appended claims should not be limited to the description of the preferred embodiments contained herein.

EXAMPLES

The following examples are provided for illustrative purposes only and are not to be construed as limiting the invention's scope in any manner.

Example 1

A composition of the present invention is described in Table 2 below.

| Ingredient | Weight | Weight percent |
|---|---|---|
| Morphine sulfate pentahydrate | 122.6 mg | 0.2 |
| Lidocaine hydrochloride monohydrate | 65.4 mg | 0.06 |
| Poloxamer 407 | 20 g | 19.3 |
| Edetate disodium dihydrate | 100 mg | 0.1 |
| Benzalkonium chloride (50% aqueous solution) | 30 mg | 0.03 |
| Sterile water | 80 g | 77.4 |
| 0.1 N aqueous hydrochloric acid | 3 g | 2.9 |

Morphine sulfate pentahydrate (122.6 mg), lidocaine (65.4 mg) hydrochloride monohydrate, and edetate disodium dihydrate (100 mg) were dissolved in 80 g of sterile water. The resulting solution was cooled to 10° C. in an ice bath and poloxmer 407 (20 g) was slowly added with mixing until the Poloxmer 407 completely dissolved. The solution was maintained at about 10° C. until the foam collapsed. About 4 g of the solution was added to a 5 ml vial and a Valois VP7/90 18/415 pump was screwed onto the vial and refrigerated at 4° C. for 30 minutes. The vial was removed from the refrigerator and the metered pump was primed using the Valois 165 actuator. The Valois 165 actuator was removed and the filled vial was stored at 4° C. until the foam collapsed. The vial was removed from the refrigerator and kept at room temperature (25° C.) until the contents gelled.

The viscosity of the above-prepared oral spray was measure using a Brookfield RVT viscometer. At 30° C. the viscosity was 82,666 cps (averaged over three determinations) and at 40° C. the viscosity was 95,666 cps (averaged over three determinations).

The composition can be applied as follows. Attach the long throat actuator to the metering pump and store the unit at 4° C. for at least 30 minutes. To prime the pump (7–8 sprays), with actuator in the up position, press the actuator firmly and quickly to spray into a waste container, hold the actuator for about one second when it is in the pressed position following each spray. With actuator in the up position, press the actuator firmly and quickly to spray onto the surface of the subject to be treated. Hold the actuator for two to three seconds when it is in the pressed position following each spray. Apply a total of 16 spray shots of for a total application of about 2 mg morphine sulfate and about 1 mg lidocaine hydrochloride in about 1.5 g of composition. Once the spray makes contact with the mucous membrane at body temperature, the liquid will form a viscous mucoadhesive gel. If it takes more than 90 seconds to apply 16 spray shots, store the unit at 4° C. for 10 minutes to cool the content before further usage.

Example 2

A second composition of the present invention is described in Table 2 below.

| Ingredient | Weight | Weight percent |
| --- | --- | --- |
| Morphine sulfate pentahydrate | 490.5 mg | 0.48% |
| Lidocaine hydrochloride monohydrate | 261.5 mg | 0.25% |
| Poloxamer 407 | 20 g | 19.4% |
| Edetate disodium dihydrate | 100 mg | 0.097 |
| Benzalkonium chloride (50% aqueous solution) | 30 mg | 0.029% |
| Sterile water | 80 g | 77.6% |
| 0.05 N aqueous hydrochloric acid | 2.2 g | 2.1% |

Morphine sulfate pentahydrate (490.48 mg), lidocaine (261.6 mg) hydrochloride monohydrate, and edetate disodium dihydrate (100 mg) were dissolved in 80 g of sterile water. The resulting solution was cooled to 10° C. in an ice bath and poloxmer 407 (20 g) was slowly added with mixing until the Poloxmer 407 completely dissolved. The solution was maintained at about 10° C. until the foam collapsed. About 4 g of the solution was added to a 5 ml vial and a Valois VP7/90 18/415 pump was screwed onto the vial and refrigerated at 4° C. for 30 minutes. The vial was removed from the refrigerator and the metered pump was primed using the Valois 165 actuator. The Valois 165 actuator was removed and the filled vial was stored at 4° C. until the foam collapsed. The vial was removed from the refrigerator and kept at room temperature (25° C.) until the contents gelled.

The viscosity of the above-prepared oral spray was measure using a Brookfield RVT viscometer. At 30° C. the viscosity was 81,000 cps (averaged over three determinations) and at 40° C. the viscosity was 94,333 cps (averaged over three determinations).

The composition can be applied using a long-throat actuator as described above (for spray application) or by cannula (for application to a specific area). A total of 4 spray shots is recommended. For application to a specific area by cannula rather than as a spray, the preferred actuator is a stainless-steel cannula of about 73 mm in length, for example, the 215 stainless-steel cannula commercially available from Valois Pharmaceuticals, Inc.

The foregoing has outlined rather broadly the more pertinent and important features of the present invention. While it is apparent that the invention disclosed herein is well calculated to fulfill the objects stated above, it will be appreciated that numerous modifications and embodiments may be devised by those skilled in the art. Therefore, it is intended that the appended claims cover all such modifications

What is claimed is:

1. A composition comprising a mucoadhesive, a local anesthetic or a pharmaceutically-acceptable salt thereof, and an opioid or a pharmaceutically-acceptable salt thereof, wherein the mucoadhesive is a block copolymer of ethylene oxide and propylene oxide.

2. The composition of claim 1, wherein an amount of the local anesthetic is within a range of from about 0.01 percent to about 0.5 percent of a total weight of the composition.

3. The composition of claim 1, wherein an amount of the opioid is within a range of from about 0.05 percent to about 1 percent of a total weight of the composition.

4. The composition of claim 1, wherein an amount of the mucoadhesive is within a range of from about 0.1 percent to about 40 percent of a total weight of the composition.

5. The composition of claim 4, wherein an amount of the mucoadhesive is within a range of from about 15 percent to about 25 percent of a total weight of the composition.

6. The composition of claim 1, wherein the mucoadhesive is a block copolymer of ethylene oxide and propylene oxide of a formula I:

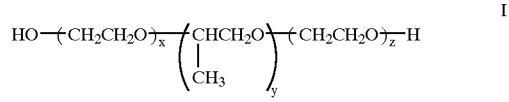

wherein x is an integer having an average value ranging from about 2 to about 128; y is an integer having an average value ranging from about 14 to about 80; and z is an integer having an average value ranging from 2 to about 128.

7. The composition of claim 1, wherein the mucoadhesive is poloxamer 407.

8. The composition of claim 1, wherein the local anesthetic is lidocaine, tetracaine, bupivacaine, prilocaine, mepivacaine, procaine, chloroprocaine, ropivacaine, dibucaine, etidocaine, benzocaine, a pharmaceutically-acceptable salt thereof, or a mixture thereof.

9. The composition of claim 8, wherein the local anesthetic is lidocaine or a pharmaceutically-acceptable salt thereof.

10. The composition of claim 1, wherein the opioid is morphine or loperamide or a pharmaceutically-acceptable salt thereof.

11. The composition of claim 10, wherein the opioid is morphine or a pharmaceutically-acceptable salt thereof.

12. A container adapted for topical application containing a composition comprising a mucoadhesive, a local anesthetic or a pharmaceutically-acceptable salt thereof, and an opioid or a pharmaceutically-acceptable salt thereof, wherein the mucoadhesive is a block copolymer of ethylene oxide and propylene oxide.

13. The container of claim 12, packaged in association with instructions, the instructions comprising: topically applying the composition onto a mucous membrane of a subject.

14. The container of claim 12, wherein the mucoadhesive is a block copolymer of ethylene oxide and propylene oxide of a formula I:

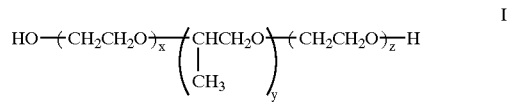

wherein x is an integer having an average value ranging from about 2 to about 128; y is an integer having an average value ranging from about 14 to about 80; and z is an integer having an average value ranging from 2 to about 128.

15. The container of claim 12, wherein the mucoadhesive is poloxamer 407.

16. The container of claim 12, wherein the local anesthetic is lidocaine, tetracaine, bupivacaine, prilocaine, mepivacaine, procaine, chloroprocaine, ropivacaine, dibucaine, etidocaine, benzocaine, a pharmaceutically-acceptable salt thereof, or a mixture thereof.

17. The container of claim 16, wherein the local anesthetic is lidocaine or a pharmaceutically-acceptable salt thereof.

18. The container of claim 12, wherein the opioid is morphine or loperamide or a pharmaceutically-acceptable salt thereof.

19. The container of claim 18, wherein the opioid is morphine or a pharmaceutically-acceptable salt thereof.

20. A method of inducing local anesthesia in a subject comprising topically applying a composition comprising a mucoadhesive, a local anesthetic or a pharmaceutically-acceptable salt thereof, and an opioid or a pharmaceutically-acceptable salt thereof to a subject, wherein the mucoadhesive is a block copolymer of ethylene oxide and propylene oxide.

21. The method of claim 20, wherein the composition is applied to the buccal mucous membrane.

22. The method of claim 20, wherein an amount of the local anesthetic is within a range of from about 0.01 percent to about 0.5 percent of a total weight of the composition.

23. The method of claim 20, wherein an amount of the opioid is within a range of from about 0.05 percent to about 1 percent of a total weight of the composition.

24. The method of claim 20, wherein an amount of the mucoadhesive is within a range of from about 0.1 percent to about 40 percent of a total weight of the composition.

25. The method of claim 24, wherein an amount of the mucoadhesive is within a range of from about 15 percent to about 25 percent of a total weight of the composition.

26. The method of claim 20, wherein the mucoadhesive is a block copolymer of ethylene oxide and propylene oxide of a formula I:

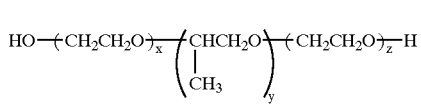

wherein x is an integer having an average value ranging from about 2 to about 128; y is an integer having an average value ranging from about 14 to about 80; and z is an integer having an average value ranging from 2 to about 128.

27. The method of claim 20, wherein the mucoadhesive is poloxamer 407.

28. The method of claim 20, wherein the local anesthetic is lidocaine, tetracaine, bupivacaine, prilocaine, mepivacaine, procaine, chloroprocaine, ropivacaine, dibucaine, etidocaine, benzocaine, a pharmaceutically-acceptable salt thereof, or a mixture thereof.

29. The method of claim 28, wherein the local anesthetic is lidocaine or a pharmaceutically-acceptable salt thereof.

30. The method of claim 20, wherein the opioid is morphine or loperamide or a pharmaceutically-acceptable salt thereof.

31. The method of claim 30, wherein the opioid is morphine or a pharmaceutically-acceptable salt thereof.

* * * * *